United States Patent [19]

Smit

[11] Patent Number: 4,602,886
[45] Date of Patent: Jul. 29, 1986

[54] MULTI-COLOR MARKING IMPLEMENT

[76] Inventor: Adrianus J. Smit, DeWetstein Pfisterlaan 22, 3971 BW Driebergen, Netherlands

[21] Appl. No.: 564,839

[22] Filed: Dec. 28, 1983

[51] Int. Cl.$^4$ .............................................. B43K 27/00
[52] U.S. Cl. .......................................... 401/35; 401/49
[58] Field of Search ...................... 401/35, 49, 69, 79; 264/73, 74, 75, 76, 77

[56] References Cited

U.S. PATENT DOCUMENTS

| | | |
|---|---|---|
| 209,154 | 10/1878 | Bill . |
| 471,191 | 3/1892 | Prewitt . |
| 800,338 | 9/1905 | Streuli . |
| 1,075,880 | 10/1913 | Walls .................................. 401/35 |
| 1,475,579 | 11/1923 | Harlan . |
| 2,101,540 | 12/1937 | Gullich . |
| 2,434,477 | 1/1948 | Winter . |
| 2,481,019 | 9/1949 | Joyce . |
| 2,776,051 | 1/1957 | Warren, Jr. . |
| 3,201,314 | 8/1965 | Morshauser et al. ................. 167/85 |
| 3,279,999 | 10/1966 | Harrison et al. ...................... 401/49 |
| 3,287,484 | 11/1966 | Justus . |
| 3,479,429 | 11/1969 | Morshauser et al. ................. 424/63 |
| 4,208,144 | 6/1980 | Idec et al. . |

FOREIGN PATENT DOCUMENTS

| | | |
|---|---|---|
| 592701 | 2/1960 | Canada . |
| 585556 | 3/1925 | France ................................. 401/79 |
| 49-41389 | 11/1974 | Japan . |
| 51-86141 | 7/1976 | Japan . |
| 6515437 | 7/1966 | Netherlands . |
| WO82/0044-44 | 7/1981 | PCT Int'l Appl. . |

Primary Examiner—Steven A. Bratlie
Attorney, Agent, or Firm—Kenyon & Kenyon

[57] ABSTRACT

This application discloses multi-color marking implements (i.e. crayons) having variegated color patterns, and a method and apparatus for their manufacture involving consecutively casting small amounts of molten crayon-like materials into suitably shaped molds at specific temperatures. The marking implements have a multiplicity of discretely-colored regions of random shape, randomly distributed in the implement. In addition, the marking implement may include a multiplicity of non-discretely colored regions resulting from a blending of colors from two discretely-colored regions. Optionally, the multi-color implement may be provided in a transparent lipstick type container that may serve as the mold in the casting process.

13 Claims, 12 Drawing Figures

MULTI-COLOR MARKING IMPLEMENT

BACKGROUND OF THE INVENTION

The present invention relates to multi-color, solid masses having an essentially random color distribution, specifically to marking instruments and implements, and to a method and apparatus for their manufacture. More particularly, this invention relates to a multi-color, crayon-type marking implement.

Implements capable of making marks of more than one color are known.

International Patent Application No. PCT/GB81/00150 (Publication No. WO 82/00444) (Carrington) discloses a drawing implement comprising a plurality of colored layers formed one above the other by laminar casting, i.e., one layer cast onto another.

U.S. Pat. No. 471,191 issued Mar. 22, 1892 discloses a layered crayon of different colors.

U.S. Pat. No. 2,101,540 issued Dec. 7, 1937 discloses a compressed-powder article molded into a plurality of profiled layers.

In addition, Dutch Patent Application No. 65/15437 discloses multi-colored cosmetic preparations such as eye shadows and lipsticks.

SUMMARY OF THE INVENTION

It is an object of the present invention to provide multi-colored solid masses in which the colors are randomly distributed in the mass.

It is another object of the present invention to provide multi-colored solid masses in which the colors exist in both discrete regions and regions of blended colors.

It is another object of the present invention to provide such multi-colored solid masses which can be used to apply the colors of the mass to a surface, preferably in a random pattern so that a single stroke of such a mass leaves a unique track or mark of random colors on the stroked surface.

It is another object of the present invention to provide a solid, multi-colored marking instrument or implement in which the colors are randomly distributed in the marking implement.

It is another object of the present invention to provide a crayon-like, multi-color marking implement in which the colors are randomly distributed throughout the implement.

It is another object of the present invention to provide such a crayon-like implement having both discretely-colored regions and blended, i.e. non-discretely-colored, regions.

It is another object of the present invention to provide such marking instruments and implements, particularly a crayon-like implement, capable of simultaneously applying a plurality of colors in a generally random pattern to a marking surface.

It is yet another object of the present invention to provide methods and apparatus for efficiently and economically manufacturing the solid masses and marking instruments and implements mentioned above.

The above and other objects are achieved by the invention disclosed herein.

The invention provides a multi-colored, solid mass of material comprising a multiplicity of substantially discretely-colored material regions of at least two, and preferably more than three, different colors adhered together into the solid mass. The discretely-colored material regions are more or less randomly shaped and substantially randomly distributed in the solid mass.

The multi-colored solid mass is useful as a marking implement, among other things.

Preferably the multi-colored mass may further include a multiplicity of substantially non-discretely-colored material regions blended of at least two colors. The non-discretely-colored material regions are comprised of the different colored materials from at least two discretely-colored regions and typically occur at the interface between contiguous discretely-colored regions. Since the non-discretely-colored regions are between the discretely-colored regions, they are similarly randomly shaped and randomly distributed.

In one embodiment of the invention, a multi-colored mass of discretely-colored regions of ten different colors and non-discretely-colored regions is provided. The non-discretely-colored regions are preferably comprised of different colored materials from at least two discretely-colored regions adjacent to which the respective non-discretely-colored region is located.

The shape of a substantial number of discretely-colored regions randomly varies along at least two axes. According to one embodiment, the regions are distributed along a longitudinal axis.

The volume of each of the discretely-colored regions is preferably about 0.1 to about 0.2 cc and more preferably about 0.153 cc., including portions of any non-discretely-colored regions which comprise a portion of a non-discretely-colored region. Of course, the volume may be varied as desired to achieve various artistic effects.

The solid mass according to one embodiment is shaped in the form of a solid cylinder having a total volume of about 10 cc. and is a marking implement, which is preferably disposed in a lipstick-type container.

A multi-color marking implement of the present invention comprises a body made up of a plurality of essentially randomly-disposed discrete color regions or portions, that is, a variegated mass, of at least two colors and preferably as many as ten or more colors. Preferably, the implement includes non-discretely-colored regions which are described above.

The discretely- and non-discretely colored regions are made of materials such as meltable crayon-like substances that are solid at room temperatures, e.g., wax, and may have some color themselves and/or include a coloring agent such as a pigment or dye. According to an embodiment, the materials include waxes, non-drying mineral oils and pigments or dyes. Preferably, the marking implement includes non-discretely-colored portions, as described above, and the materials are each cast at a specified temperature to control, among other things, material flow and color blending between contiguous colored materials.

According to the method of the invention, a multi-colored solid mass as described above is made. The method comprises providing molten wax-like materials of at least two different colors; dispensing a metered amount of a first material maintained at a first temperature into a mold; and after a predetermined cooling period, dispensing a metered amount of a material of different color from the first into the mold at a second temperature so that the two dispensed materials at least partially form discrete material regions. The above steps are repeated a multiplicity of times to form the solid adhered mass.

Preferably, metered amounts of molten materials of at least two different colors are repeatedly dispensed while each material is at a selected temperature, and a predetermined cooling period separates consecutive dispensings of materials.

The materials are preferably sequentially dispensed, although they can be randomly dispensed or dispensed in cyclically changing or random sequences.

The predetermined cooling period may be selected so that portions of at least two consecutively dispensed materials blend to form a non-discretely-colored region of a third color or tone, or a blend of colors.

According to one embodiment, the pigments or dyes are preferably selected to form colors from the group consisting of yellow, dark blue, orange, purple, red, green, light blue, pink, carmin red and salmon, which are preferably cast at the following temperatures: yellow 80° C., dark blue 80° C., orange 105° C., purple 75° C., red 75° C., green 85° C., light blue 90° C., pink 80° C., carmin red 65° C., and salmon 80° C.

Much to his surprise, the applicant has found that dispensing the different materials at different temperatures, and controlling the quantity dispensed and the time period between consecutive dispensings, can produce a solid multi-colored mass with a substantially controlled amount of blending at the interface of the consecutively dispensed materials. This blended region is referred to herein as a non-discretely-colored region since the blending of colors produces further colors and tones distinguishable from the discrete colors of which they are composed.

The applicant has further found that the size of and blending degree in these interface regions can be controlled by controlling one or more of the above process parameters. The applicant has thus found it surprising and unexpected to produce a solid mass having both discretely-colored regions and non-discretely-colored regions substantially randomly distributed in the mass. Moreover, the color patterns obtainable are indeed surprising given that the shape of the regions can be random, their distribution in the mass random, and the large number of tones and patterns of blended colors obtainable. For example, using only ten different colors, the applicant has been able to provide a solid mass having hundreds and even thousands of color patterns, tones, etc.

According to one embodiment, the combinations are cast into a cylindrical mold having a concave base to form a marking implement.

Apparatus according to the invention for carrying out the method of the invention comprises a plurality of molding stations, each station having a plurality of nozzles for injecting molten wax-like material into a plurality of molds; means for transferring the molten wax-like material to the nozzles at desired temperatures and discharging metered amounts therefrom into the molds; and means for relatively moving the nozzles and molds so that selected molds are sequentially advanced from one nozzle to another for receiving metered amounts of molten wax-like material therefrom.

According to one embodiment, the means for relatively moving the nozzles and molds is a rotating table with the molds disposed in a spaced relation thereon. Each molding station comprises a material reservoir for holding a material of a different color, means for maintaining the material in the reservoir at a desired temperature, means for conducting the mixture to the nozzles and means for metering the material dispensed from the nozzles.

Preferably, the molds are disposed on the table along spaced radii thereof and the molding stations are disposed circumferentially above the rotating table. The spacing between the molding stations exceeds the spacing between adjacent radii along which the molds are disposed so that molds disposed along at least one radii will not be at a molding station while molds along another radii are disposed at the molding station. This arrangement enables the material in molds not under a molding station to cool. Control of the indexing and dwell times of the table, and the number of radii along which molds are disposed and the number of molding stations will determine the cooling time for each dispensed quantity of material.

The above and other objects, features, aspects and advantages of the present invention will be more readily perceived from the following description of the preferred embodiments thereof when considered with the accompanying drawings and appended claims.

BRIEF DESCRIPTION OF THE DRAWINGS

The present invention is illustrated by way of example, and not limitation, in the figures of the accompanying drawings in which like numerals indicate similar parts and in which.

DESCRIPTION OF THE PREFERRED EMBODIMENTS

Figures 1, 2, 4, 5:
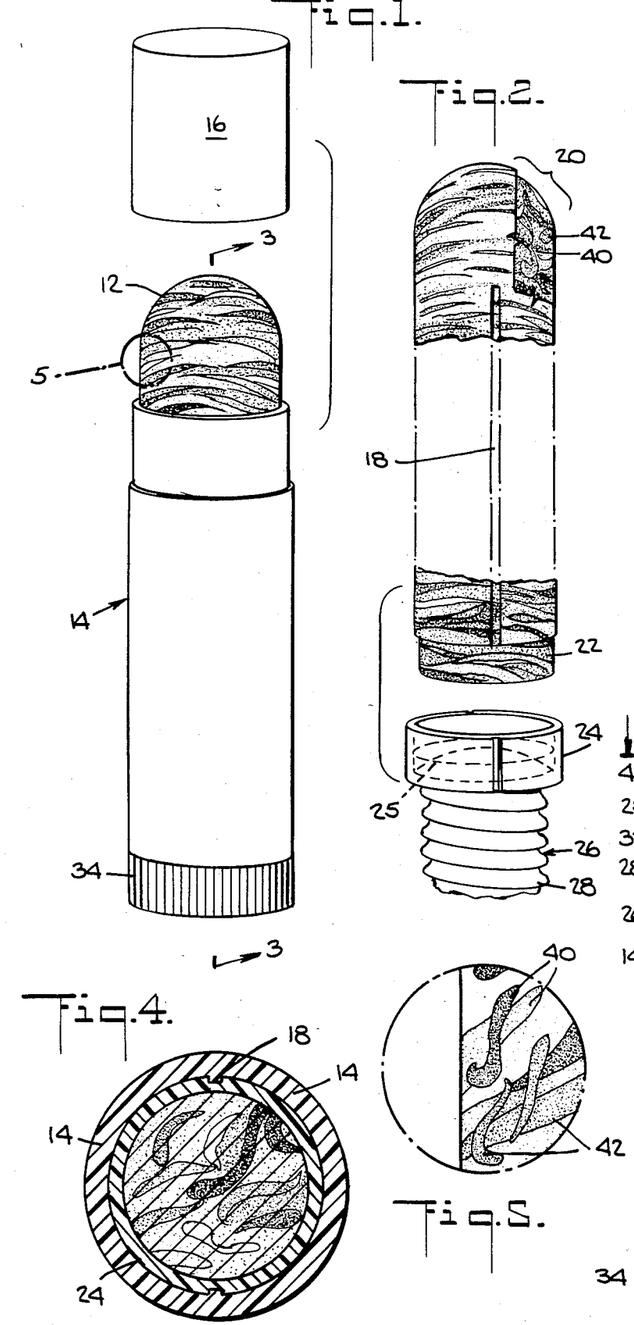
FIG. 1 is a perspective view of a marking implement constructed in accordance with the present invention secured in a lipstick-type container shown with its cap removed.
FIG. 2 is an exploded perspective view, partially in longitudinal cross-section, of the marking implement of FIG. 1 and the base to which it is secured.
FIG. 4 is a cross sectional view of the marking implement and container of FIG. 1 taken along line 4—4 of FIG. 3.
FIG. 5 is a partial, radial cross-sectional view of the implement of FIG. 1.

A preferred product of the present invention is illustrated in FIG. 1 and comprises a marking implement body 12 for simultaneously applying a plurality of colors having a variegated color pattern as described herein.

The marking implement body 12 may be conveniently disposed in a lipstick type, preferably transparent, container 14 provided with cooperating cap 16 to prevent accidental marking and reduce deterioration of the implement body 12 by exposure to air. The implement body 12 as shown in FIG. 2 is preferably provided with at least one longitudinal groove 18 for orientating it in the lipstick container 14 and a smooth or rounded top 20 so that it produces an even mark when applied to a paper or like surfaces. The lower end 22 of the implement body 12 is securely engaged in seat 24 which is provided with an annular inwardly protruding ring 25 to insure secure attachment to the implement body 12 and with screw means 26 having threads 28.

Figure 3:
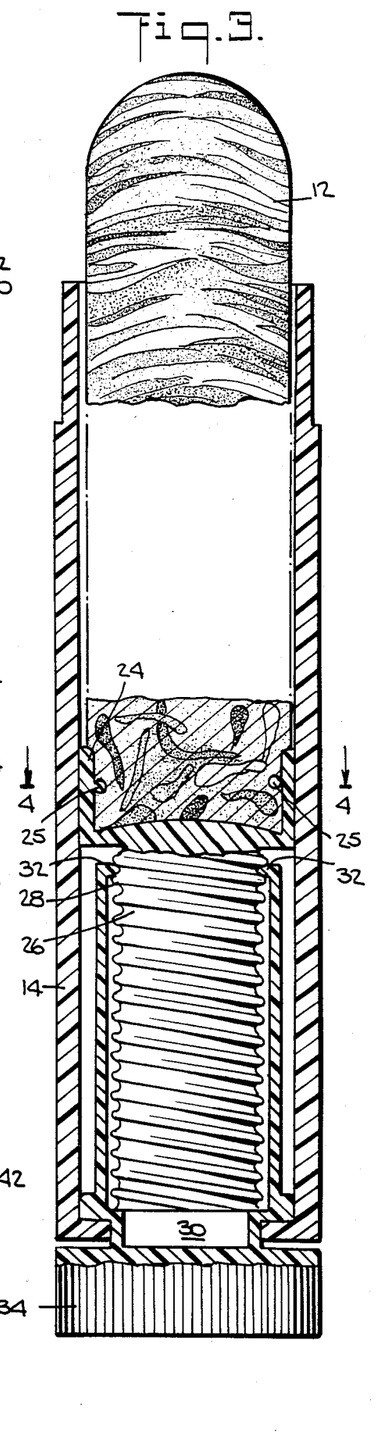
FIG. 3 is an enlarged cross-sectional view of the marking implement and container of FIG. 1 taken along line 3—3 of FIG. 1.

The screw means 26 acts cooperatively with a rotatable member 30 so that threads 28 ride on protrusions 32 as seen in FIG. 3. When knob 34 is rotated in one direction, the threads 28 ride along protrusions 32 advancing the implement 12 out of the tubular portion of the container 14 for use. Similarly, when knob 34 is rotated in the opposite direction, implement 12 is drawn into the container 14 for storage.

In FIG. 5 the variegated color pattern of implement body 12 is illustrated along a horizontal plane and in FIG. 2 the variegated color pattern is illustrated along a vertical plane.

As shown, in FIGS. 4 and 5, the implement body 12 comprises a multiplicity of randomly shaped regions referenced generally by 40. Each region is substantially discretely-colored, i.e. it has relatively definite boundaries as to a specific color. The regions 40 are sufficiently adhered to each other to form the solid implement body 12. As shown in FIG. 2, the regions are substantially randomly distributed. In addition, between some regions there is an interface region, designated generally by 42, in which color from two or more adjacent regions is blended. These regions 42 are therefore substantially non-discrete as to a specific color. The method disclosed herein enables the formation of such an implement.

The materials of which the implement is made comprise waxes, non-drying mineral oils and pigments or dies. The materials can also include soaps. The composition of the particular materials used will depend on the particular colors desired and other properties. Such materials are known in the art and are available from Konlinklijke Talens BV, Sophialaan 46, 7300 AA Apeldoorn, Netherlands, for example.

Figure 6:
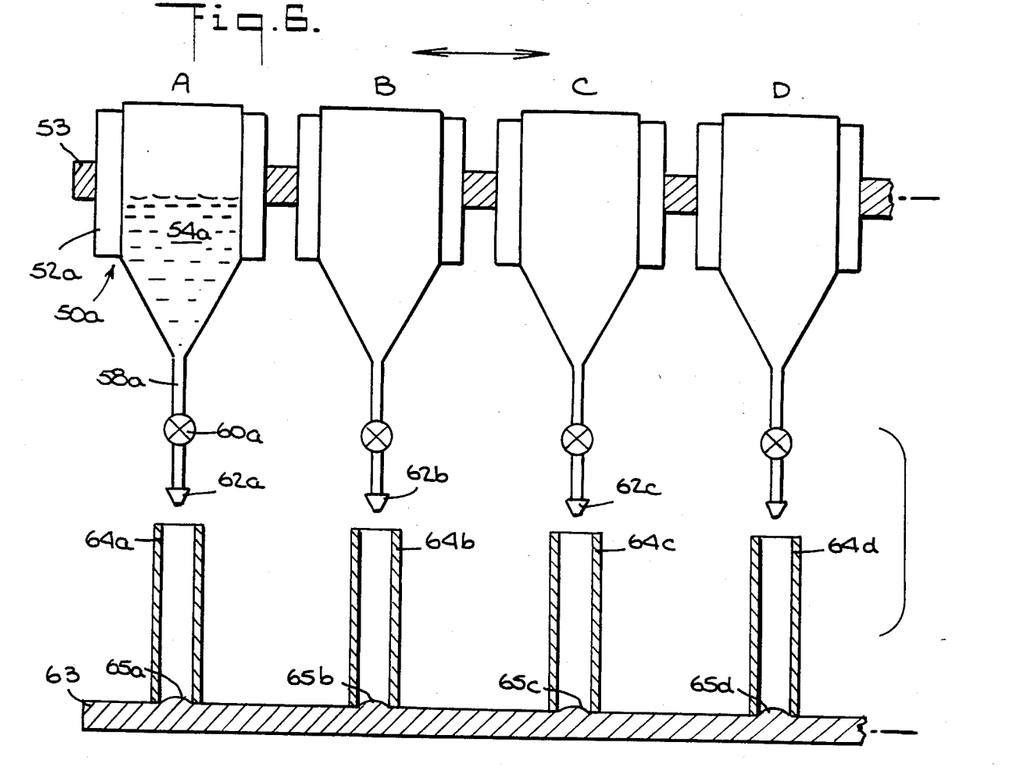
FIG. 6 is a schematic view of an apparatus constructed in accordance with the present invention which is effective to carry out the method of the invention.

FIG. 6 is a schematic representation of the method of the present invention and the cooperating means therefor. The four dispensing units A, B, C and D snown in FIG. 6 are structurally identical and for convenience like parts in each such unit are identified by the same reference numerals differentiated by subscripts a, b, c and d, and only the structure and operation of dispensing unit A will be described herein. It will be appreciated by those skilled in the art that in an actual manufacturing machine almost any number of dispensing units can be used.

Hopper 50a is a thermally controlled receptical for colored molten material 54a such as a non-toxic composition or crayon-like material composed of pigment dispersed in mixtures of waxes and non-drying mineral oils and, optionally modifying additives such as soaps to render the material washable. The composition and physical properties of these materials are known in the art as indicated above. Hopper 50a may be provided with agitator means (not shown) as necessary or desired to maintain the homogeneity of molten material 54a. Heating means 52a, e.g. an electric resistance heater, is provided in close thermal communication with the hopper 50a and is further adapted to accurately control the temperature of molten material 54a therein and as it egresses therefrom via outlet conduit 58a. Metering means 60a is an electromechanical valve, or the like, for regulating the flow of molten material 54a thru conduit 58a so that selected quantities, i.e. doses, are intermittently expelled from nozzle 62a into mold means 64a disposed therebelow.

While the hydrostatic head of molten material 54a is usually sufficient to move material through the dosing unit A, a pressure assist means for this purpose may be provided where necessary or desirable as is known in the art. The dispensing units are disposed on frame 53 in spaced relation to each other as dictated by the positions of corresponding mold means on table 64 a, b, c. . . Either frame 53 or table 63, or both, may be provided with a carriage means (not shown) for moving each relative to the other so that the various molding means may be brought into alignment with different nozzles to receive doses of molten material therefrom as shown in FIGS. 7-9.

Figure 7:
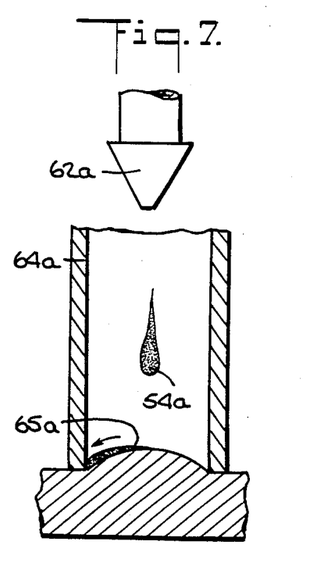
FIGS. 7, 8, and 9 are schematic views illustrating the consecutive casting process of the present invention as carried out by the apparatus of FIG. 6.
Figure 8:
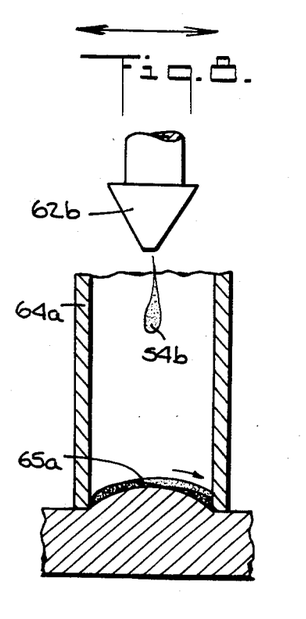
Figure 9:
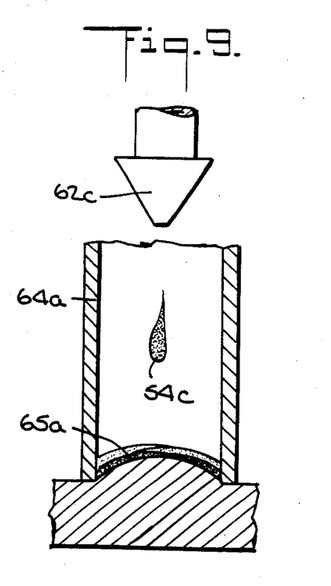

FIGS. 7-9 illustrate a typical dosing cycle which involves aligning nozzle 62a with mold means 64a at which time the metering means 60a is triggered by a suitable controller to expel a small dose of molten material 54a, which in this case has a red color, into the cylindrical hollow of mold means 64a. The red molten material 54a comes to rest, cools, and solidifies at the bottom 65a of mold 64a which is preferably of convex shape to aid in spreading the molten material 54a.

The mold means 64a is thereafter moved i.e., indexed, into alignment with nozzle 62b, as shown in FIG. 8 and the above described dosing cycle is repeated causing a dose of molten material 54b, having a blue color, to issue from nozzle 62b into mold means 64a. The dose of blue molten material 54b comes to rest, cools, and solidifies at the bottom 65a of mold means 64a. Of course as the process progresses the bottom portion of each mold will be defined by previous doses of molten material.

The mold means 64a is thereafter indexed into alignment with nozzle 62c, as shown in FIG. 9, and the described dosing cycle is again repeated depositing a dose of green molten material 54c on the cooling red and blue doses 54a and 54b, respectively.

The dosing cycle is repeated over and over again as the mold means advances from dosing unit to dosing unit until a solid mass comprising an implement body of the desired size and shape having a variegated color pattern is built up. The mass may be removed from the mold means by any well known technique.

In practice the various colors in the implement body formed from the molten material are cast in accordance with the above described consecutive casting technique at specified temperatures controlled by the heating means, to produce a variegated color pattern wherein each dose produces a discretely-colored region. Preferably, a controlled amount of color blending occurs at the interface between various doses which produces additional colors in the resulting non-discretely-colored regions.

Preferred temperatures of the molten materials for producing highly desired color patterns are:

| 1. | Yellow | 90° C. |
| 2. | Dark Blue | 70° C. |
| 3. | Orange | 105° C. |

| | -continued | |
|---|---|---|
| 4. | Purple | 75° C. |
| 5. | Red | 75° C. |
| 6. | Green | 85° C. |
| 7. | Light Blue | 90° C. |
| 8. | Pink | 70° C. |
| 9. | Carmin Red | 65° C. |
| 10. | Salmon | 80° C. |

The above list of temperatures is merely representative of the differences in temperature required to produce the multi-color implements of this invention. Specific temperatures for a given application will be determined by the composition of the materials used, their viscosity at specific temperatures, to a limited extent the desired random shape, distribution and blending of colored regions, the thermal properties of the apparatus, e.g. the forming mold, and the like. The required temperatures may be empirically determined.

The cooling periods which occur between injection of doses into the mold and to a certain extent some of the factors mentioned above determine the degree to which non-discretely-colored blending regions are formed. Shorter cooling periods in which a prior dose is still relatively molten will produce larger blended regions while longer cooling periods will tend to diminish blending of consecutive doses so that any non-discretely-colored regions formed will be relatively small.

The discretely- and non-discretely-colored regions are shown to extend along two principal axes, horizontal and vertical. By proper selection of molds and dispensing nozzles, the regions could extend along other axes, for example spherical axes. Moreover, it is possible to alter the distribution of the colored regions by movement of the mold receptacles during injection and/or cooling of the molten materials.

The quantity of material dispensed also plays a part in defining the random shape of the region. Larger quantities will tend to flow more and blend with other doses, while smaller quantities will tend to solidify faster. Preferably, for a cylindrical marking implement having a diameter of about 2 cm, the doses are about 0.1 to above 0.2 cc in volume. In a preferred embodiment, the doses are about 0.153 cc in volume and the implement has a total volume of about 10 cc.

Figure 10:
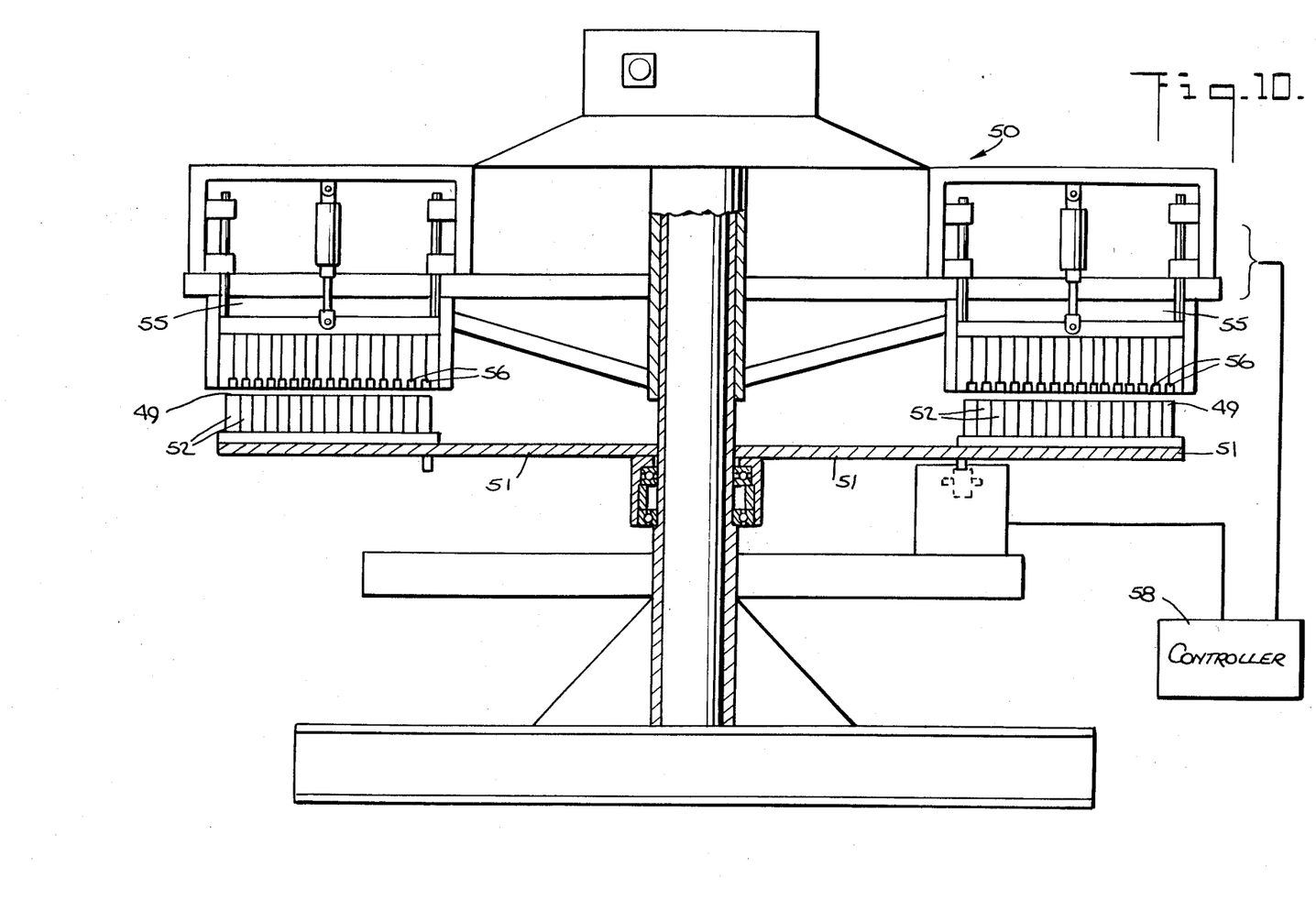
FIG. 10 is a schematic, vertical section view of one embodiment of a rotary table apparatus according to the invention for carrying out the method of the invention.
Figure 11:
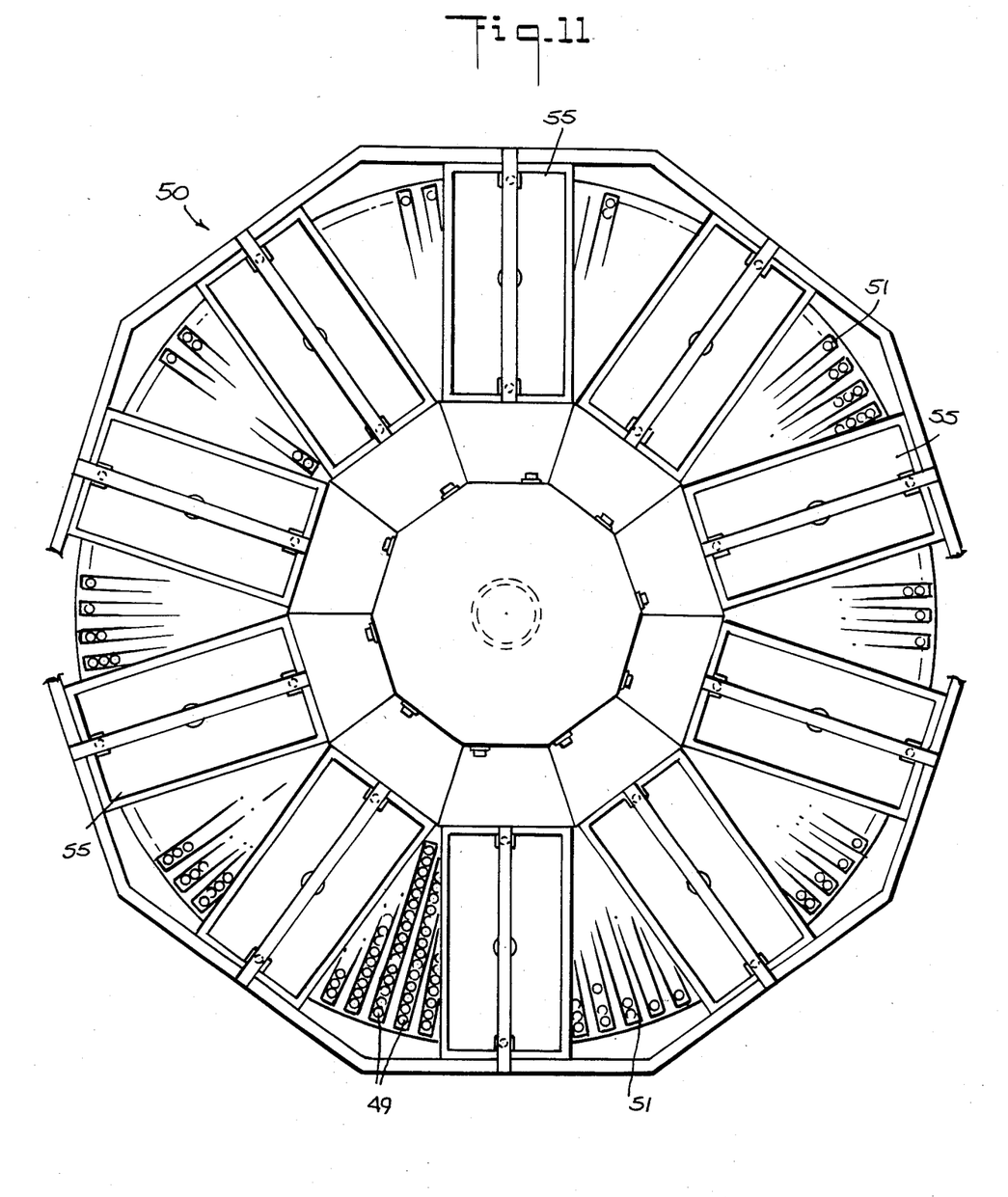
FIG. 11 is a schematic top plan view of the apparatus of FIG. 10.

Referring now to FIGS. 10 and 11, an embodiment of an automated apparatus 50 for mass producing the implement of the invention is depicted. The apparatus includes a rotatable table 51 having a multiplicity of receptacles 52 for receiving removable cylindrical molds 49 in the form of lipstick-type containers. The receptacles 52 are aligned along a multiplicity of spaced radii, for example spaced 3.6 degrees apart so that 100 rows of receptacles are provided. Each row can contain as many as 16 receptacles, or more. The table is conventionally rotatably supported.

Supported above the table 51 are ten vats 55 which serve as reservoirs for ten different colored materials. The vats are stationary, extending circumferentially above the table. The central axes of the vats are spaced 36° apart. Each vat is provided with a heating element, for example an electric heater, which precisely controls the temperature of the material in the vat and may optionally be provided with agitation means described above. Each vat is also provided with 16 injection nozzles 56 from which the molten material is dispensed. The nozzles 56 and receptacles 52 are correspondingly radially spaced. Means not shown are provided to meter predetermined amounts of material dispensed from the nozzles during each dwell period of the table. Control means which can include a microcomputer are provided in control center 58 to regulate indexing of the table and timing for dispensing molten material from the nozzles.

In operation, the table is stopped during a dwell period with ten rows of receptacles disposed below respective vats and corresponding nozzles. Molten material is then dispensed into the molds in the respective rows. Only two to three drops, i.e. about 0.153 cc, of material need be dispensed to produce a single discretely-colored region. The table is next indexed so another ten rows of receptacles are disposed under the respective vats and molten material is dispensed into the molds of those rows. Meanwhile, the material injected into molds now between vats is cooling. The number of rows of receptacles, and index and dwell timing is adjusted so that a desired cooling period, for example about 40–42 seconds, is obtained. The cycle described above sequentially continues until each mold has been injected a multiplicity of times with molten material from each vat and a solid mass having a variegated color pattern as described herein is obtained. It will be appreciated that the required cooling between doses of molten material is dependent on the temperatures of the molten material, surrounding temperatures, the thermal properties of the mold, etc. and that each can be varied with respect to the other to achieve the necessary cooling.

The marking implement 12 is preferably produced in the container in which it will be sold. The convex portion of seat 24 in the container 14 imparts a convex curved end 20 to the finished implement body 12 that is useful for marking smooth even lines with the implement as described above. A gap which provides clearance between the container 14 and the implement body 12 cast therein, is provided by the shrinkage that the molten material undergoes on cooling. A sufficient gap is typically formed after about 15 minutes cooling at about 18° C. This clearance is necessary to permit the implement to slide freely in the container when knob 34 is rotated.

Figure 12:
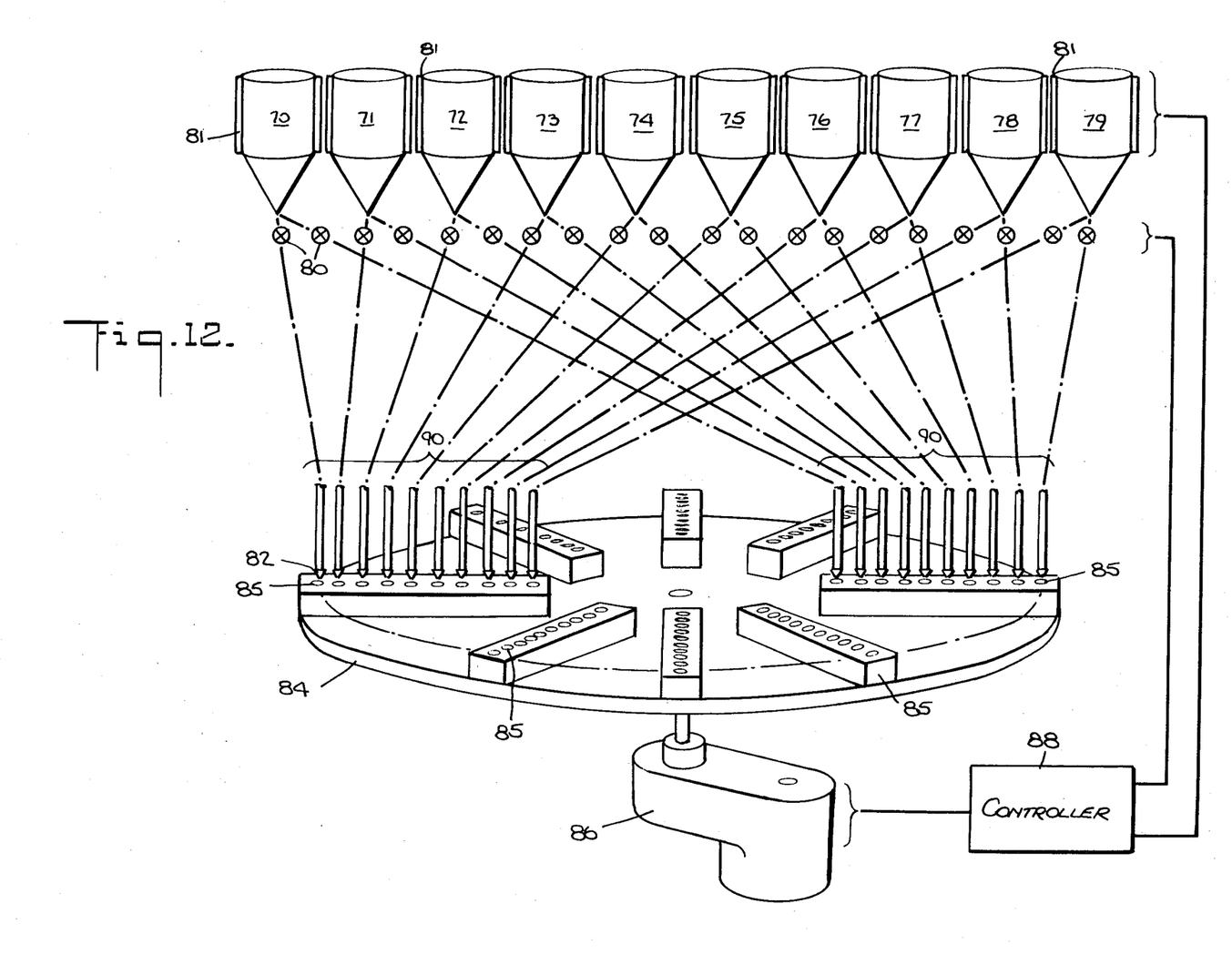
FIG. 12 is a schematic view of another embodiment of a rotary table apparatus for carrying out the method of the invention.

FIG. 12 illustrates another embodiment of the apparatus for manufacturing marking implements and carrying out the method of the present invention. The apparatus includes ten thermostacially controlled hoppers 70–79 each containing molten material of a different color maintained at the preferred temperatures listed above by electric heaters 81. Each hopper is provided with eighteen outlet conduits 80 and corresponding nozzles 82 (although only two are shown in FIG. 12 for purposes of clarity) which are controlled by metering means as previously described with reference to FIGS. 6 thru 9. Thus doses of molten color material can be injected into one hundred and eighty (180) molds at one time. Rotating table 84 is provided with motor means 86 and controller 88 for indexing mold seats 85 arranged thereon in circular paths from one nozzle 82 to another so that the molds are aligned with the nozzles to receive predetermined doses e.g. about 3 drops of different molten color materials. The mold seats 85 in this embodiment are annular openings adapted to frictionally engaging the lower exterior portion of a lipstick type container 14 as shown in FIG. 1, without cap 16. The lipstick-type containers 14 serve as the mold cavity in this embodiment also. The doses of colored molten material are introduced directly into the containers 14 via nozzles 82 which are arranged in an array, resembling spokes in a wheel, on rotating table 84. The 180 nozzles are arranged into ten dosing stations at selected positions so that they may be simultaneously aligned with groups of containers 14 to be dosed. Additional groups of molding seats 85 (not shown) loaded with containers 14 are provided in similar arrangement between those positioned at the ten dosing stations 90 so that a time interval between dosings necessary for adequate solidification of the molten materials, e.g. 40–42 seconds, is obtained. An electromechanical controller means 88 preferably directed by a microcomputer or the like, coordinates the movement of table 85 and the operation of the metering means 80. Thus each container is automatically advanced from one nozzle 82 to another for successively receiving separate doses of predetermined amounts of colored molten material at selected temperatures, on desired time intervals, until a solid mass having a variegated color pattern of the desired size is built up in containers 14.

Each mark left by an implement of the invention is unique in itself. The various colors of the multi-color mass are presented to a drawing surface, such as paper, so that they are rubbed off onto the surface in a random pattern dictated by the arrangment of the discretly-colored regions and the non-discretely-colored regions of the implement, as well as, the mixing of those colors on the surface. The implement of the invention permits infinite artistic possibilities not heretofore known.

Certain changes and modifications of the embodiments of the invention disclosed herein will be readily apparent to those skilled in the art. It is the applicant's intention to cover by his claims all those changes and modifications which could be made to the embodiments of the invention herein chosen for the purpose of disclosure without departing from the spirit and scope of the invention.

What is claimed is:

1. A multi-colored marking implement comprising a multiplicity of substantially discretely-colored material regions of at least two different colors molded together into a solid mass comprising a crayon-like material, the material regions being substantially randomly distributed in the solid mass and including a multiplicity of distinct substantially non-discretely-colored material regions blended from and between at least two discretely-colored material regions, the non-discretely-colored material regions being substantially randomly shaped and substantially randomly distributed in the solid mass, such that when the implement is marked on a drawing surface completely random multi-colored patterns are produced, said patterns exhibiting color from the discretely and non-discretely colored material regions.

2. The multi-colored solid mass according to claim 1 including a multiplicity of substantially discretely-colored material regions of three or more different colors which are substantially randomly shaped and substantially randomly distributed in the solid mass.

3. The multi-colored solid mass according to claim 2 including a multiplicity of substantially non-discretely-colored material regions blended from at least two of said three colors, the non-discretely-colored material regions being substantially randomly shaped and substantially randomly distributed in the solid mass.

4. The multi-colored solid mass according to claim 3 where the non-discretely-colored material regions are comprised of different colored materials from at least two discretely-colored regions adjacent to which the respective non-discretely-colored region is located.

5. The multi-colored solid mass according to claim 4 wherein there are ten different colors.

6. The multi-colored solid mass according to claim 1 wherein the shape of a substantial number of discretely-colored regions randomly varies along at least two axes.

7. The multi-colored solid mass according to claim 1 wherein the solid mass is shaped in the form of a solid cylinder.

8. The combination of a multi-colored solid mass according to claim 7 and a lipstick-type container to which the solid cylindrical mass is axially movably secured.

9. The combination according to claim 8 wherein the lipstick-type container includes inner and outer coaxially arranged members, the cylindrical mass being secured to the inner member, means for relatively axially moving the members from a retracted position in which the solid mass is surrounded by the outer member and a use position in which the solid mass protrudes from the outer member, the outer member being transparent.

10. The combination according to claim 9 wherein the inner member includes an arcurate base in which the cylindrical mass is secured.

11. The multi-colored solid mass according to claim 1 wherein a substantial number of discretely-colored regions each has a volume of about 0.1 to 0.2 cc.

12. The multi-colored solid mass according to claim 1 wherein the regions are distributed along a longitudinal axis of the mass.

13. The multi-colored solid mass according to claim 1 wherein the discretely-colored material regions each comprise a mixture of waxes and non-drying mineral oils, the regions further comprising one of at least two pigments or dyes or combinations thereof to provide the at least two different colors, the multi-colored solid mass being useful as a marking implement.

* * * * *

UNITED STATES PATENT AND TRADEMARK OFFICE
CERTIFICATE OF CORRECTION

PATENT NO. : 4,602,886

DATED : July 29, 1986

INVENTOR(S) : Adrianus J. Smit

It is certified that error appears in the above-identified patent and that said Letters Patent is hereby corrected as shown below:

In the Abstract, line 13, change "lipstick type" to --lipstick-type--.

Column 3, line 16, change "carmin" to --carmine--.

Column 3, line 20, change "carmin" to --carmine--.

Column 5, line 49, change "snown" to --shown--.

Column 5, line 58, change "receptical" to --receptacle--.

Column 5, line 62, change "optionally" to --optional--.

Column 6, line 6, change "thru" to --through--.

Column 7, line 7, change "Carmin" to --Carmine--.

Column 8, line 46, change "thermostacially" to --thermostatically--.

Column 8, line 54, change "thru" to --through--.

UNITED STATES PATENT AND TRADEMARK OFFICE
CERTIFICATE OF CORRECTION

PATENT NO. : 4,602,886

DATED : July 29, 1986

INVENTOR(S) : Adrianus J. Smit

It is certified that error appears in the above-identified patent and that said Letters Patent is hereby corrected as shown below:

Column 9, line 24, change "discretly" to --discretely--.

Column 9, line 51, change "surface completely" to --surface, completely--.

Column 10, line 13, change "where" to --wherein--.

Column 10, line 38, change "arcurate" to --arcuate--.

Signed and Sealed this

Second Day of February, 1988

Attest:

DONALD J. QUIGG

*Attesting Officer*     *Commissioner of Patents and Trademarks*